US00PP18379P2

(12) United States Plant Patent
Van Zanten

(10) Patent No.: US PP18,379 P2
(45) Date of Patent: Jan. 1, 2008

(54) *CHRYSANTHEMUM* PLANT NAMED 'GG GOFRT 05'

(50) Latin Name: *Chrysanthemum morifoluim*
Varietal Denomination: GG GOFRT 05

(75) Inventor: Leo Van Zanten, Oxnard, CA (US)

(73) Assignee: G + G Breeding Corporation, Oxnard, CA (US)

( * ) Notice: Subject to any disclaimer, the term of this patent is extended or adjusted under 35 U.S.C. 154(b) by 0 days.

(21) Appl. No.: 11/395,076

(22) Filed: Mar. 31, 2006

(51) Int. Cl.
*A01H 5/00* (2006.01)

(52) U.S. Cl. ..... Plt./298

(58) Field of Classification Search ..... Plt./297, Plt./298
See application file for complete search history.

(56) References Cited

PUBLICATIONS

Brummit, R.K.; "The Garden"; "Chrysanthemum once again," Sep. 1997; pp. 662–663. (2 pages total).*

* cited by examiner

*Primary Examiner*—Kent Bell
*Assistant Examiner*—S. B. McCormick-Ewoldt

(57) ABSTRACT

A new and distinct *Chrysanthemum* plant cultivar is disclosed, characterized by small daisy type inflorescences, consistent flowering response to short days, blooming consistently after 52 days of short day length, dark lavender ray florets, and a moderate branching habit.

1 Drawing Sheet

Latin name of the genus and species: *Chrysanthemum morifolium.*
Variety denomination: 'GG GOFRT 05'.

BACKGROUND OF THE INVENTION

The new cultivar 'GG GOFRT 05' was originated from a cross made by Leo Van Zanten in a planned breeding program in December 2001 between the unpatented male parent 'Elgon' and the unpatented female parent 'Tasman'. The new cultivar was discovered and selected by Leo Van Zanten in October 2002 in Oxnard, Calif.

Asexual reproduction of the new cultivar 'GG GOFRT 05' by vegetative cuttings was performed in Oxnard, Calif., and has shown that the unique features of this new cultivar are stable and reproduced true to type on successive generations.

SUMMARY OF THE INVENTION

The cultivar 'GG GOFRT 05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG GOFRT 05'. These characteristics in combination distinguish 'GG GOFRT 05' as a new and distinct *Chrysanthemum* cultivar:

1. Small daisy type inflorescence;
2. Dark lavender ray florets;
3. Moderate branching habit; and
4. Blooming consistently after 52 days of short day length.

Plants of the new cultivar 'GG GOFRT 05' are similar to plants of the male parent 'Elgon' in most horticultural characteristics, however plants of the new cultivar 'GG GOFRT 05' have more yellow-green foliage than the parent. Also, 'GG FRT 05' has more lavender color ray florets than the red-purple ray florets of the parent and 'GG FRT 05' has a smaller inflorescence diameter.

Plants of the new cultivar 'GG GOFRT 05' are similar to plants of the female parent 'Tasman' in most horticultural characteristics, however plants of the new cultivar 'GG GOFRT 05' has dark lavender ray florets compared to the white florets of the female parent. Also, 'GG FRT 05' is smaller in both height and plant spread. Finally, 'GG FRT 05' has smaller leaves and smaller inflorescences.

In comparison to the commercially available variety 'Davis' (U.S. Plant Pat. No. 7,325), 'GG GOFRT 05' is smaller in height. Additionally, the new variety 'GG GOFRT 05' has more true green foliage and more lavender-purple than the red-purple ray florets of 'Davis.' Further, the new variety 'GG GOFRT 05' has smaller inflorescences.

BRIEF DESCRIPTION OF THE PHOTOGRAPH

The accompanying photograph in FIG. 1 illustrates in full color a typical plant of 'GG GOFRT 05' grown in a 6.5-inch container. Five cuttings were used in the pot, planted late October and grown in a greenhouse. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG GOFRT 05' plants grown in Oxnard, Ventura County, Calif., during the winter months. The growing temperature in the greenhouse from 67° F. and 78° F. Measurements and numerical values represent averages of typical flowering types.

Botanical classification: *Chrysanthemum morifolium* cultivar 'GG GOFRT 05.'
Commercial classification: Pot-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 23 cm.
Plant spread: Approximately 30 cm.
Growth rate: Moderate.
Branching characteristics: Moderate branching.
Length of lateral branches: Approximately 18 cm.
Number of leaves per lateral branch: Approximately 34.
Age of plant described: Approximately 98 days.

FOLIAGE

Leaf:
*Arrangement.*—Alternate single.
*Average length.*—Approximately 3.7 cm.
*Average width.*—Approximately 2.6 cm.
*Shape of blade.*—Ovate.
*Apex.*—Acuminate.
*Base.*—Attenuate.
*Attachment.*—Stalked.
*Margin.*—Palmately lobed, sinuses between lateral lobes parallel to divergent.
*Texture of top surface.*—Lightly pubescent.
*Texture of bottom surface.*—Lightly pubescent.
*Leaf internode length.*—Approximately 1.5 cm.
*Color.*—Young foliage upper side: Near Green 137A. Young foliage under side: Near Green 137C. Mature foliage upper side: Near Green 137A. Mature foliage under side: Near Green 137D.
*Venation.*—Type: Palmately net. Venation color upper side: Near Green 137A. Venation color under side: Near Green 137D.
Petiole:
*Average length.*—Approximately 1.3 cm.
*Color.*—Near Green 138A.
*Diameter.*—Approximately 0.2 cm.

BLOOM

Inflorescence:
*Flowering habit.*—Induced by darkness period greater than 13.5 hours, approximately 52 days of appropriate day length required to induce and develop blooms.
*Inflorescence form.*—Daisy.
*Number of inflorescences per lateral branch.*—Approximately 15.
*Inflorescence diameter.*—Approximately 4 cm.
*Inflorescence depth.*—Approximately 1.3 cm.
*Inflorescence longevity on plant.*—Approximately 35 to 42 days.
*Persistence.*—Persistent.
*Fragrance.*—None detected.
Ray florets:
*Appearance.*—Matte.
*Texture.*—Smooth.
*Average number of ray florets per florescence.*—20.
*Number of whorls.*—Approximately 2.
*Shape.*—Oblanceolate.
*Aspect.*—Flat.
*Margin.*—Entire.
*Apex.*—Obtuse.
*Length.*—Approximately 1.2 cm.
*Width.*—Approximately 0.8 cm.
*Color.*—Upper surface at first opening: Near Red-Purple 70A. Upper surface at maturity: Near Purple 78C but closer to Red-Purple 62A on the edge of the ray floret. Upper surface at fading: Near Purple 77D. Under surface at first opening: Near Purple 77C. Under surface at maturity: Near Purple 75C. Under surface at fading: Near Purple 76C.
Disc florets:
*Appearance.*—Matte.
*Texture.*—Smooth.
*Average number of florets per disc.*—Approximately 160.
*Shape.*—Cylindric.
*Apex.*—Obtuse.
*Average length.*—Approximately 0.2 cm.
*Average width.*—Approximately 0.1 cm.
*Color.*—At first opening: Near Yellow-Green 154A. At maturity: Near Yellow-Green 145A. At fading: Near Green-Yellow 1B.
Peduncle:
*Length.*—At terminal end (shortest): Approximately 2.6 cm. At lateral end (longest): Approximately 4.5 cm.
*Angle to stem.*—Acute.
*Strength.*—Moderate.
*Color.*—Near Green 138B.
*Habit.*—Upright.
*Diameter.*—Approximately 0.1 cm.
*Surface texture.*—Lightly pubescent.
Inflorescence bud:
*Length.*—Approximately 0.4 cm.
*Diameter.*—Approximately 0.8 cm.
*Form.*—Globular.
*Color.*—Near Yellow-Green 145C.
Involucral bracts (phyllaries):
*Appearance.*—Matte.
*Texture.*—Lightly pubescent.
*Number.*—Approximately 20.
*Shape.*—Ovate.
*Margin.*—Entire.
*Apex.*—Acute.
*Length.*—Approximately 0.5 cm.
*Width.*—Approximately 0.3 cm.
*Color.*—Upper side: Near Green 137A. Under side: Near Green 137B.

REPRODUCTIVE ORGANS

Ray florets:
*Number of pistils per floret.*—1.
*Stigma shape.*—2 branched.
*Stigma color.*—Near Yellow 9A.
*Style color.*—Near Yellow-Green 149C.
*Style length.*—Approximately 0.4 cm.
*Stamens.*—Absent.
Disc florets:
*Number of pistils per floret.*—1.
*Stigma shape.*—Cylindric.
*Stigma color.*—Near Yellow 9A.

*Style length.*—Approximately 0.2 cm.
*Style color.*—Near Yellow-Green 154D.
*Number of stamens per floret.*—Approximately 5.
*Anther shape.*—Tubular.
*Anther color.*—Near Yellow 9A.
*Pollen color.*—Near Yellow 9A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/Seed production: Commercially, this plant is not used or observed in a stage where seeds would be produced. Therefore, seed production has not been observed.

What is claimed is:

1. A new and distinct cultivar of *Chrysanthemum* plant named 'GG GOFRT 05' as herein illustrated and described.

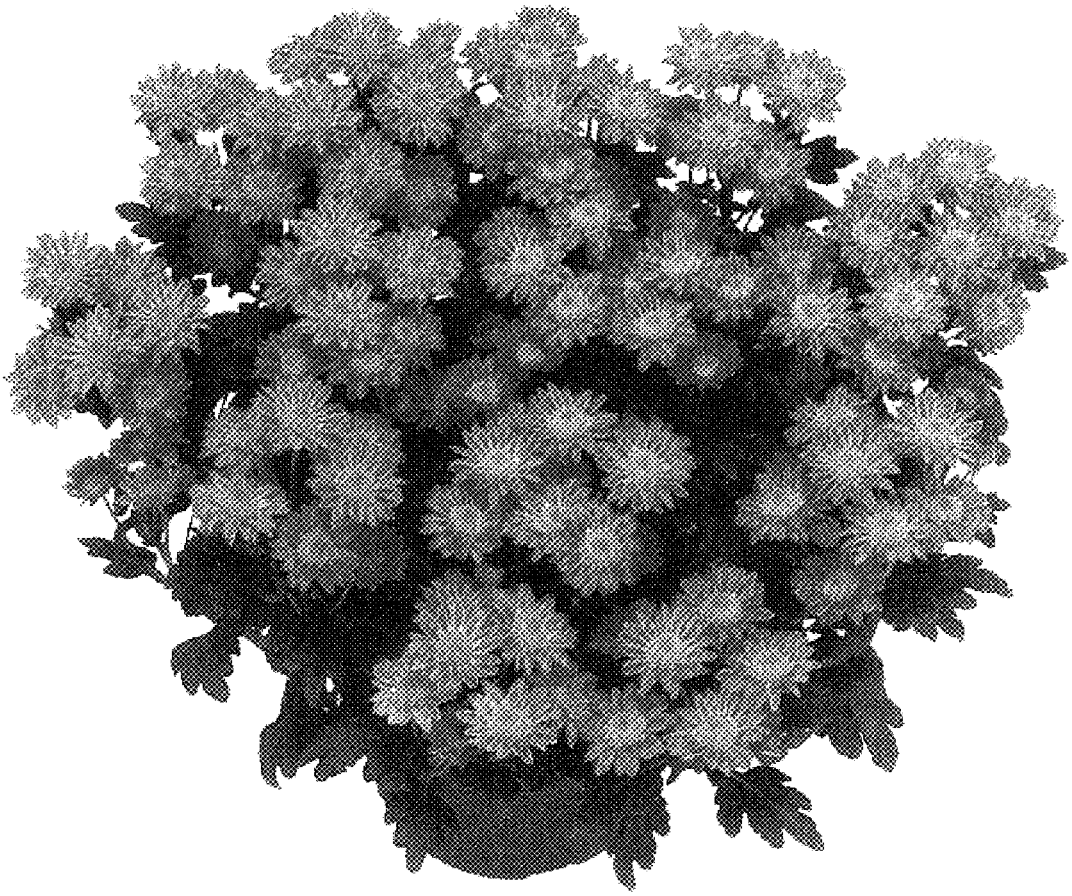

* * * * *